(12) United States Patent
Epps et al.

(10) Patent No.: US 6,818,413 B2
(45) Date of Patent: Nov. 16, 2004

(54) FLUORESCENCE-BASED HIGH THROUGHPUT SCREENING ASSAYS FOR PROTEIN KINASES AND PHOSPHATASES

(75) Inventors: Dennis E. Epps, Kalamazoo, MI (US); Charles K. Marschke, Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/600,815

(22) Filed: Jun. 20, 2003

(65) Prior Publication Data

US 2003/0235865 A1 Dec. 25, 2003

Related U.S. Application Data

(62) Division of application No. 09/731,428, filed on Dec. 6, 2000, now Pat. No. 6,630,311, which is a division of application No. 09/204,335, filed on Dec. 2, 1998, now Pat. No. 6,203,994.
(60) Provisional application No. 60/067,833, filed on Dec. 5, 1997.

(51) Int. Cl.$^7$ ............................................. G01N 33/573
(52) U.S. Cl. .............................. 435/7.4; 435/15; 435/4; 435/7.5; 435/7.7; 435/968; 435/7.92; 435/7.94; 435/287.2; 436/517; 530/350; 530/352; 530/23.4
(58) Field of Search .......................... 435/15, 7.4, 7.5, 435/4, 7.7, 968, 7.92, 7.94, 287.2; 436/517; 530/350, 352, 23.4

(56) References Cited

U.S. PATENT DOCUMENTS

| | | | |
|---|---|---|---|
| 4,681,859 A | 7/1987 | Kramer | 436/501 |
| 5,070,025 A | 12/1991 | Klein et al. | 436/546 |
| 5,759,787 A | * 6/1998 | Strulovici | 435/7.4 |
| 5,912,137 A | * 6/1999 | Tsien et al. | 435/15 |

FOREIGN PATENT DOCUMENTS

| | | | |
|---|---|---|---|
| WO | WO93/03377 | 2/1993 | G01N/33/573 |
| WO | WO95/18823 | 7/1995 | C07K/7/06 |
| WO | WO97/42501 | 11/1997 | G01N/33/53 |
| WO | WO98/18956 | 5/1998 | C12Q/1/42 |

OTHER PUBLICATIONS

Dandliker, WB et. al., "Equilibrium and Kinetic Inhibition Assays Based Upon Fluorescence Polarization," Methods in Enzymology, 74:3–28 (1997).
Owicki, JC, et. al. "Application of Fluorescence Polarization Assays in High–Throughput Screening," Genetic Engineering News, 17:27 (1997).
Krishna Seethala, "A Fluorescence Polarization Tyrosine Kinase Assay for High Throughput Screening," 3$^{rd}$ Annual Conference of the Society for Biomolecular Screening, San Diego, CA, Sep. 22–25.
Checovich, WJ, et. al., Nature, 375:254–256 (1995).
T. Hunter, Cell, 80:225–236 (1995).
Levine, LM, et. al., Anal. Biochem., 247:83–88 (1997).
Rotman, B., et. al., Proc. Natl. Acad. Sci., 50:1–6 (1963).
Zhang, Z–Y, et. al., Analytical Biochemistry, 211:7–15 (1993).

* cited by examiner

*Primary Examiner*—Christopher L. Chin
*Assistant Examiner*—Pensee T. Do
(74) *Attorney, Agent, or Firm*—Edward F. Rehberg; Lori K. Kerber

(57) ABSTRACT

The invention relates to novel fluorescence-based assays for protein kinases and phosphatases which can be used in high throughput screening. The methods of the invention utilize a competitive immunoassay to determine the amount of substrate that is phosphorylated or dephosphorylated during the course of a kinase or phosphatase reaction to yield a product, as well as the phosphorylating or dephosphorylating activity of a kinase or phosphatase.

26 Claims, 7 Drawing Sheets

Figure 1
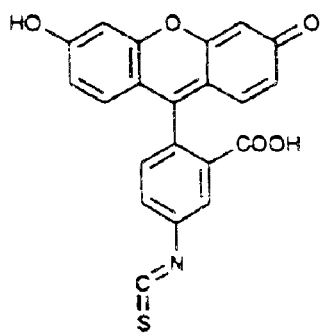
5-Fluorescein Isothiocyanate (Isomer I)
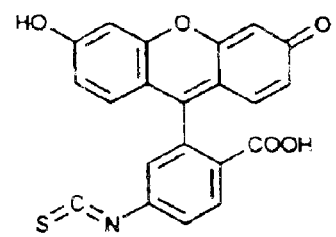
6-Fluorescein Isothiocyanate (Isomer II)
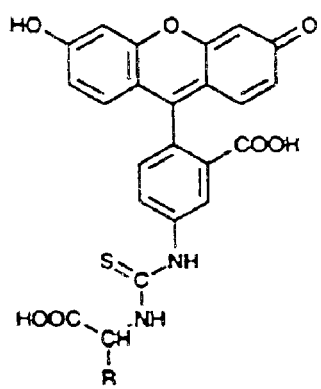
5-Fluorescein Phosphoryl Amino Acid (Isomer I Derivative)
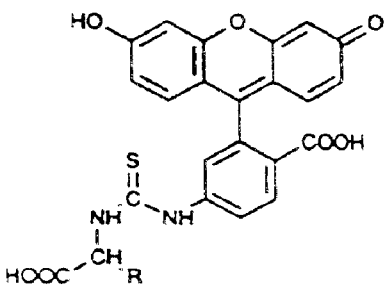
6-Fluorescein Phosphoryl Amino Acid (Isomer II)
Phosphoryl Tyrosine R = 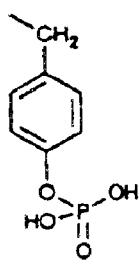
Phosphoryl Serine R = 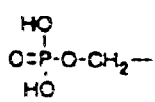
Phosphoryl Threonine R = 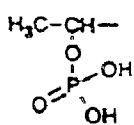

Figur 6
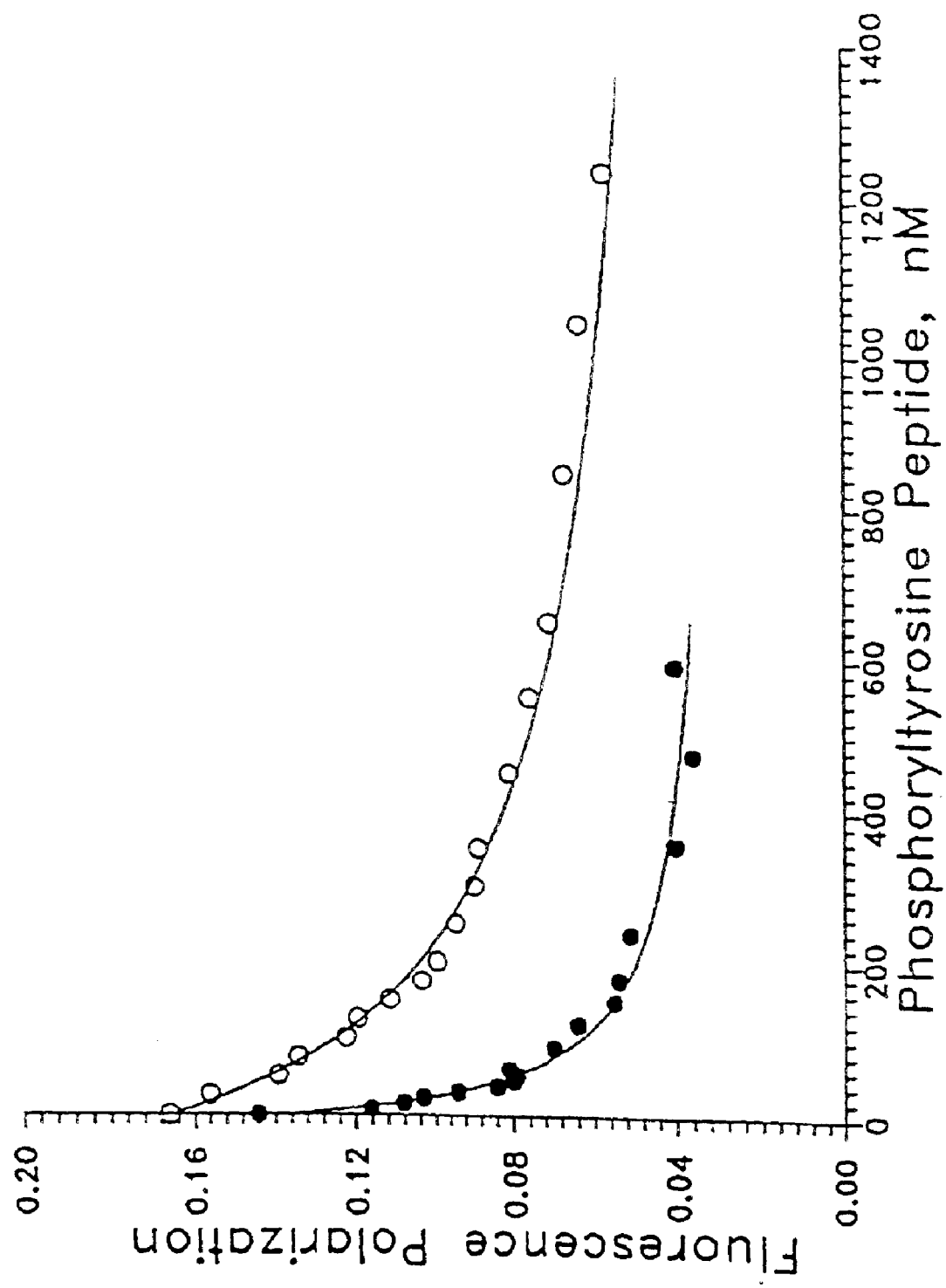

FLUORESCENCE-BASED HIGH THROUGHPUT SCREENING ASSAYS FOR PROTEIN KINASES AND PHOSPHATASES

CROSS-REFERENCE TO RELATED APPLICATIONS

This application is a divisional of U.S. Application Ser. No. 09/731,428 filed Dec. 6, 2000 now U.S. Pat. No. 6,630,311, which is a divisional of U.S. application Ser. No. 09/204,335 now U.S. Pat. No. 6,203,994 filed Dec. 2, 1998, which claims the benefit of U.S. Provisional Application No. 60/067,833, filed 5 Dec. 1997.

FIELD OF THE INVENTION

The invention relates to novel fluorescence-based assays for kinases and phosphatases which can be used in high throughput screening.

BACKGROUND OF THE INVENTION

Eukaryotes employ phosphorylation and dephosphorylation of specific proteins to regulate many cellular processes (T. Hunter, Cell 80:225–236 (1995); (Karin, M., Curr. Opin. Cell Biol. 3:467–473 (1991)). These processes include signal transduction, cell division, and initiation of gene transcription. Thus, significant events in an organism's maintenance, adaptation, and susceptibility to disease are controlled by protein phosphorylation and dephosphorylation. These phenomena are so extensive that it has been estimated that humans have around 2,000 protein kinase genes and 1,000 protein phosphatase genes (T. Hunter, Cell 80:225–236 (1995)), some of these likely coding for disease susceptibility. For these reasons, protein kinases and phosphatases are good targets for the development of drug therapies.

The most frequently used protein kinase and phosphatase screens employ either radioactive ATP or ELISAs. However, the use of radioactive ATP is undesirable due to the attendant costs of record-keeping, waste-disposal, and the fact that the assay format is not homogeneous. ELISAs are undesirable because they have a lower assay throughput due to the extra steps required for both washing and the enzyme reaction.

Fluorescence detection in the visible wavelengths offer an alternative to the use of radiotracers or ELISAs for kinase and phosphatase assays, as fluorescence offers detection limits comparable to those of radioactivity. Furthermore, this eliminates the cost of radioactive waste disposal. For example, the change in absorbance and fluorescence spectra of phosphotyrosine which occurs upon dephosphorylation has been used for the continuous monitoring of protein-tyrosine phosphatase (PTP) activity (Zhao, Z. et al., Anal. Biochem. 202:361–366 (1993)). However, previously developed fluorometric assays for kinases and phosphatases have not been especially amenable to the requirements of high throughput screening.

Fluorescence detection frequently offers the advantage of using homogeneous assay formats (i.e.—"mix, incubate, and read"). Indeed, the high throughput screening (HTS) field is moving rapidly toward the use of fluorescence, luminescence, absorbance, and other optical methods. Two fluorescence techniques, fluorescence polarization (FP) and fluorescence resonance energy transfer (FRET) are finding widespread use for assays, both in the private sector for HTS, secondary assays including kinetics, SAR studies, etc., and in university laboratories. The use of FP is particularly desirable since its readout is independent of the emission intensity (Checovich, W. J., et al., Nature 375:254–256 (1995); Dandliker, W. B., et al., Methods in Enzymology 74:3–28 (1981)) and is thus insensitive to the presence of colored compounds that quench fluorescence emission. FRET, although susceptible to quenching, can also be used effectively, especially for continuous enzyme assays.

From the forgoing, it will be clear that there is a continuing need for the development of cost-effective, facile, and sensitive optical kinase and phosphatase assays for both high throughput screening (HTS) and secondary assays.
Information Disclosure Checovich, W. J., et al., Nature 375:254–256 (1995).

Dandliker, W. B., et al., Methods in Enzymology 74:3–28 (1981).

E. Harlow and D. Lane, eds., Antibodies A Laboratory Manual, Cold Spring Harbor Laboratory (1988).

T. Hunter, Cell 80:225–236 (1995).

Leavine, L. M., et al., Anal. Biochem. 247:83–88 (1997).

Owicki, J. C., Genetic Engineering News 17:27 (Nov. 1, 1997).

Rotman, B., et al., Proc. Nat. Acad. Sci. 50:1–6 (1963).

Seethala, R. and R. Menzel, A Fluorescence Polarization Tyrosine Kinase Assay for High Throughput Screening, 3rd Annual Conference of The Society for Biomolecular Screening, San Diego, Calif., Sep. 22–25, 1997.

SUMMARY OF THE INVENTION

The invention relates to novel fluorescence-based assays for protein kinases and phosphatases which can be used in high throughput screening. The methods of the invention utilize a competitive immunoassay to determine the amount of substrate that is phosphorylated or dephosphorylated during the course of a kinase or phosphatase reaction to yield a product, as well as the phosphorylating or dephosphorylating activity of a kinase or phosphatase.

Thus, in one embodiment, the invention relates to a method of determining the phosphorylating activity of an enzyme comprising the steps of:

(a) combining the enzyme with
  (i) a reporter molecule comprising a fluorescent label and a phosphorylated amino acid, wherein the amino acid is selected from the group consisting of serine, threonine and tyrosine;
  (ii) a substrate molecule comprising the same amino acid that is phosphorylated in said reporter, wherein said substrate molecule is capable of being phosphorylated at said amino acid by said enzyme to yield a product;
  (iii) an antibody which selectively binds to a molecule comprising the phosphorylated amino acid; and
  (iv) a high-energy phosphate source;
(b) measuring the fluorescence polarization (FP), FQ, or fluorescence resonance spectroscopy (FCS) of the reporter following the combination of step (a); and
(c) using the FP, FQ, or FCS measurement of step (b) to determine the activity of the enzyme.

In another embodiment, the invention relates to a method for determining the dephosphorylating activity of an enzyme comprising the steps of:

(a) combining the enzyme with
  (i) a reporter molecule comprising a fluorescent label and a phosphorylated amino acid, wherein the amino acid is selected from the group consisting of serine, threonine and tyrosine;
  (ii) a substrate molecule comprising the same phosphorylated amino acid as said reporter, wherein said substrate molecule is capable of being dephosphorylated at said amino acid by said enzyme to yield a product; and
(iii) an antibody which selectively binds to a molecule comprising the phosphorylated amino acid;
(b) measuring the FP, FQ, or FCS of said reporter following the combination of step (a); and
(c) using the FP, FQ, or FCS measurement of step (b) to determine the activity of the enzyme.

The methods of the invention can also be used to determine the phosphorylation or dephosphorylation of a substrate molecule by an enzyme. Thus, in another embodiment, the invention relates to a method for determining the phosphorylation of a substrate molecule by an enzyme at an amino acid selected from the group consisting of serine, threonine and tyrosine, comprising the steps of:
(a) combining the substrate molecule with
(i) the enzyme
(ii) a reporter molecule comprising a fluorescent label and a phosphorylated amino acid, wherein the amino acid is the same amino acid which is phosphorylated in the reporter;
(iii) an antibody which selectively binds to a molecule comprising the phosphorylated amino acid; and
(iv) a high-energy phosphate source;
(b) measuring the FP, FQ, or FCS of the reporter following the combination of step (a); and
(c) using the FP, FQ, or FCS measurement of step (b) to determine whether the substrate molecule has been phosphorylated.

In another embodiment, the invention relates to a method for determining the dephosphorylation of a substrate molecule by an enzyme, wherein the substrate molecule comprises a phosphorylated amino acid, and wherein the amino acid is selected from the group consisting of serine, threonine and tyrosine, comprising the steps of:
(a) combining the substrate molecule with
(i) the enzyme;
(ii) a reporter molecule comprising a fluorescent label and a phosphorylated amino acid, wherein the reporter molecule comprises the same phosphorylated amino acid as the substrate molecule; and
(iii) an antibody which selectively binds to a molecule comprising the phosphorylated amino acid;
(b) measuring the FP, FQ, or FCS of the reporter following the combination of step (a); and
(c) using the FP, FQ, or FCS measurement of step (b) to determine whether the substrate molecule has been dephosphorylated.

In a preferred embodiment, the substrate in any of the above methods is combined with the enzyme before the addition of the reporter and the antibody. In another preferred embodiment, the substrate, the reporter, and the antibody are combined with the enzyme simultaneously.

Because the above-described methods of the invention utilize a competitive immunoassay to determine the amount of phosphorylated or dephosphorylated substrate (i.e., the amount of product) produced, the amount of phosphorylated substrate required to displace the reporter from the antibody will vary depending upon the $K_d$ of the phosphorylated substrate for the antibody and the $K_d$ of the antibody for the reporter molecule.

Thus, where the $K_d$ of the phosphorylated substrate for the antibody is, e.g., 10-fold higher than the $K_d$ of the antibody for the reporter molecule, then an amount of phosphorylated substrate ten times higher than the amount of reporter will be required for the phosphorylated substrate to displace the reporter from the antibody.

In a more preferred embodiment, the $K_d$ of the phosphorylated substrate for the antibody will be approximately equal to the $K_d$ of the antibody for the reporter molecule. In a still more preferred embodiment, the $K_d$ of the phosphorylated substrate for the antibody will be less than the $K_d$ of the antibody for the reporter molecule. In this situation, phosphorylation of the substrate will quantitatively displace the reporter from the antibody.

In accordance with the above description, one way of reducing the amount of substrate needed to displace the reporter from the antibody is to choose a reporter having a low $K_d$ for the antibody. Because anti-phosphorylamino acid antibodies may have a higher affinity for a fluorescently labeled phosphorylamino acid than for a fluorescently labeled peptide comprising the same phosphorylamino acid, in a preferred embodiment, such peptides are used as the reporter.

The methods of the invention also allow the utilization of a continuous recording assy (i.e., a "real time" assay) for the determination of either kinase or phosphatase activity by using a FRET format.

Thus, in another embodiment, the invention relates to a method of determining the phosphorylating activity of an enzyme comprising the steps of:
(a) combining the enzyme with:
(i) a substrate molecule comprising an amino acid selected from the group consisting of Ser, Thr, and Tyr, wherein said substrate molecule is capable of being phosphorylated at said amino acid by said enzyme to yield a product, and wherein said substrate molecule is labeled with an acceptor fluorophore;
(ii) an antibody which selectively binds to a molecule comprising the phosphorylated amino acid, said antibody being labeled with a donor fluorophore which corresponds to the acceptor fluorophore labeling said substrate; and
(iii) a high-energy phosphate source;
(b) measuring the FRET of the combination of step (a); and
(c) using the FRET measurement of step (b) to determine the activity of the enzyme.

In another embodiment, the invention relates to a method of determining the phosphorylating activity of an enzyme comprising the steps of:
(a) combining the enzyme with:
(i) a substrate molecule comprising an amino acid selected from the group consisting of Ser, Thr, and Tyr, wherein said substrate molecule is capable of being phosphorylated at said amino acid by said enzyme to yield a product, and wherein said substrate molecule is labeled with a donor fluorophore;
(ii) an antibody which selectively binds to a molecule comprising the phosphorylated amino acid, said antibody being labeled with an acceptor fluorophore which corresponds to the donor fluorophore labeling said substrate; and
(iii) a high-energy phosphate source;
(b) measuring the FRET of the combination of step (a); and
(c) using the FRET measurement of step (b) to determine the activity of the enzyme.

In another embodiment, the invention relates to a method of determining the dephosphorylating activity of an enzyme comprising the steps of:

(a) combining the enzyme with:
   (i) a substrate molecule comprising a phosphorylated amino acid selected from the group consisting of phosphoserine, phospothreonine and phosphotyrosine, wherein said substrate molecule is labeled with an acceptor fluorophore;
   (ii) an antibody which selectively binds to a molecule comprising the phosphorylated amino acid, said antibody being labeled with a donor fluorophore which corresponds to the acceptor fluorophore labeling said substrate; and
   (iii) a high-energy phosphate source;
(b) measuring the FRET of the combination of step (a); and
(c) using the FRET measurement of step (b) to determine the activity of the enzyme.

In another embodiment, the invention relates to a method of determining the dephosphorylating activity of an enzyme comprising the steps of:
(a) combining the enzyme with:
   (i) a substrate molecule comprising a phosphorylated amino acid selected from the group consisting of phosphoserine, phospohthreonine and phosphotyrosine, wherein said substrate molecule is labeled with a donor fluorophore;
   (ii) an antibody which selectively binds to a molecule comprising the phosphorylated amino acid, said antibody being labeled with an acceptor fluorophore which corresponds to the donor fluorophore labeling said substrate; and
   (iii) a high-energy phosphate source;
(b) measuring the FRET of the combination of step (a); and
(c) using the FRET measurement of step (b) to determine the activity of the enzyme.

In another embodiment, the invention relates to a method for determining the phosphorylation of a substrate molecule by an enzyme at an amino acid selected from the group consisting of serine, threonine and tyrosine, wherein said substrate molecule is labeled with an acceptor fluorophore, comprising the steps of:
(a) combining the substrate molecule with
   (i) the enzyme
   (ii) an antibody which selectively binds to a molecule comprising the phosphorylated amino acid, said antibody being labeled with a donor fluorophore which corresponds to the acceptor fluorophore labeling said substrate; and
   (iii) a high-energy phosphate source;
(b) measuring the FRET of the reporter following the combination of step (a); and
(c) using the FRET measurement of step (b) to determine whether the substrate molecule has been phosphorylated.

In another embodiment, the invention relates to a method for determining the phosphorylation of a substrate molecule by an enzyme at an amino acid selected from the group consisting of serine, threonine and tyrosine, wherein said substrate molecule is labeled with a donor fluorophore, comprising the steps of:
(a) combining the substrate molecule with:
   (i) the enzyme
   (ii) an antibody which selectively binds to a molecule comprising the phosphorylated amino acid, said antibody being labeled with an acceptor fluorophore which corresponds to the donor fluorophore labeling said substrate; and
   (iii) a high-energy phosphate source;
(b) measuring the FRET of the reporter following the combination of step (a); and
(c) using the FRET measurement of step (b) to determine whether the substrate molecule has been phosphorylated.

In another embodiment, the invention relates to a method for determining the dephosphorylation of a substrate molecule by an enzyme, wherein the substrate molecule comprises a phosphorylated amino acid selected from the group consisting of phosphoserine, phospohthreonine and phosphotyrosine, and wherein said substrate molecule is labeled with an acceptor fluorophore comprising the steps of:
(a) combining the substrate molecule with:
   (i) the enzyme;
   (ii) an antibody which selectively binds to a molecule comprising the phosphorylated amino acid, said antibody being labeled with a donor fluorophore which corresponds to the acceptor fluorophore labeling said substrate;
(b) measuring the FRET of the reporter following the combination of step (a); and
(c) using the FRET measurement of step (b) to determine whether the substrate molecule has been dephosphorylated.

In another embodiment, the invention relates to a method for determining the dephosphorylation of a substrate molecule by an enzyme, wherein the substrate molecule comprises a phosphorylated amino acid selected from the group consisting of serine, threonine and tyrosine, and wherein said substrate molecule is labeled with a donor fluorophore comprising the steps of:
(a) combining the substrate molecule with:
   (i) the enzyme;
   (ii) an antibody which selectively binds to a molecule comprising the phosphorylated amino acid, said antibody being labeled with an acceptor fluorophore which corresponds to the donor fluorophore labeling said substrate;
(b) measuring the FRET of the reporter following the combination of step (a); and
(c) using the FRET measurement of step (b) to determine whether the substrate molecule has been dephosphorylated.

The methods of the invention can also be used to identify an agent capable of increasing or decreasing the phosphorylating activity of an enzyme comprising the steps of:
(a) performing the above method of determining the phosphorylating activity of an enzyme in the presence and in the absence of the agent;
(b) comparing the activity of the enzyme in the presence of the agent with the activity of the enzyme in the absence of the agent to determine whether the phosphorylating activity of the enzyme in the presence of the agent is increased or decreased.

In yet another embodiment, the invention relates to a method of screening for an agent capable of increasing or decreasing the dephosphorylating activity of an enzyme comprising the steps of:
(a) performing the above method of determining the dephosphorylating activity of an enzyme in the presence and in the absence of said agent;
(b) comparing the activity of said enzyme in the presence of said agent with the activity of said enzyme in the absence of said agent to determine whether the dephosphorylating activity of said enzyme in the presence of said agent is increased or decreased.

BRIEF DESCRIPTION OF THE FIGURES

FIG. 1 shows the chemical structures of reagents used in Example 1.

FIGS. 2A, 2B, and 2C are graphs showing the binding of sigma antibodies to fluoresceinated phosphorylamino acids. Fixed concentrations of P-Tyr-F (25.8 nM)(FIG. 2A), P-Ser-F (5.9 nM)(FIG. 2B), or P-Thr-F (10 nM)(FIG. 2C) were titrated with the specific antibodies as described in Methods of Example 1. The polarization was recorded after each addition and the data analyzed using Equation 7 of Example 1 in conjunction with a nonlinear least squares fitting program. In this and subsequent figures, the solid lines represent the theoretical fits to the experimental data.

FIGS. 3A and 3B are graphs showing the binding of MBL anti-phosphotyrosine antibody to P-Tyr-F. A fixed concentration (15 nM) of P-Tyr-F was titrated with the MBL antibody as described in Methods of Example 1. The FP (FIG. 3A) and total polarized emission (FIG. 3B) were monitored during the titration. The quenching data were analyzed by nonlinear least squares fitting using Equation 7 of Example 1, and the FP data using Equation 20 of Example 1 with the values of C and $Q_c/Q_L$ calculated from Equation 7 of Example 1 substituted into it.

FIGS. 4A, 4B and 4C are graphs showing the displacement of fluoresceinated phosphorylamino acids from Sigma antibodies by the corresponding unlabelled phosphorylamino acids. Concentrations of the fluoresceinated phosphorylamino acids and the corresponding Sigma antibodies were fixed, and their displacement by the phosphorylamino acids was followed by measuring the decrease in the fluorescence polarization. The fixed concentrations were: FIG. 4A: P-Tyr-F, 1 nM and MAB, 2.05 nM sites; FIG. 4B: P-Ser-F, 1 nM and MAB, 1 nM sites; FIG. 4C: P-Thr-F, 150 nM and MAb, 150 nM sites.

FIGS. 5A and 5B are graphs showing the competitive displacement of P-Tyr-F from MBL antibody by phosphoryltyrosine as measured by FQ (FIG. 5A) and FP (FIG. 5B). MBL antibody, 7.1 nM sites and P-Tyr-F, 1.7 nM were preincubated, and displacement initiated by the addition of a concentrated solution of phosphotyrosine. The increase in emission intensity and decrease in FP were monitored as a function of added phosphoryltyrosine. The data were analyzed as described in FIG. 3.

FIG. 6 is a graph showing the competitive displacement of P-Tyr-F from Sigma antibody by phosphorylated JAK-2 kinase peptides. Sigma antibody, 2.05 nM sites and P-Tyr-F, 1 nM, were preincubated and displacement initiated as described for FIG. 5. The polarization data were analyzed as described in FIG. 3. ●--●JAK-2(a); ○--○, JAK-2(b).

FIGS. 7A, 7B, 7C, and 7D are graphs showing the competitive displacement of P-Tyr-F from MBL antibody by phosphorylated JAK-2 peptide substrates JAK-2(a) (FIGS. 7A and 7B) and JAK-2(b) (FIGS. 7C and 7D). All procedures were as described in FIG. 5. For both peptides, fixed antibody=7.1 nM sites and P-Tyr-F=1.7 nM.

DETAILED DESCRIPTION OF THE INVENTION

Figure 2A:
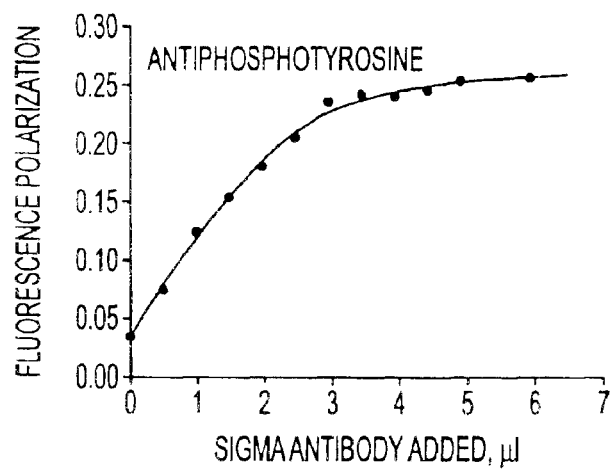
FIGS. 2A, 2B and 2C.

The invention relates to novel fluorescence-based assays for kinases and phosphatases which can be used in high throughput screening. As used herein, the term "kinase" refers to an enzyme capable of phosphorylating its substrate at a Ser, Thr, or Tyr residue, while the term "phosphatase" refers to an enzyme capable of dephosphorylating its substrate at a phosphoserine, phosphothreonine, or phosphotyrosine residue. The methods of the invention utilize a competitive immunoassay to determine the amount of phosphorylated or dephosphorylated substrate produced during the course of a kinase or phosphatase reaction, as well as the phosphorylating or dephosphorylating activity of a kinase or phosphatase. Unless otherwise indicated, "phosphorylating activity" as used herein is synonymous with "kinase activity," and "dephosphorylating activity" as used herein is synonymous with "phosphatase activity." Similarly, unless otherwise indicated, a "kinase" is defined herein as a biological material capable of phosphorylating a peptide or protein, and a "phosphatase" is defined herein as a biological material capable of dephosphorylating a peptide or protein. Further, where the enzyme used in any of the assays of the invention is a kinase, the term "phosphorylated substrate" is synonymous with "product," (i.e, the product derived from the enzymatic reaction). Similarly, where the enzyme used in any of the assays of the invention is a phosphatase, the term "dephosphorylated substrate" is synonymous with "product," (i.e, the product derived from the enzymatic reaction).

In the methods of the invention, a reporter molecule comprising a fluorescent label and a phosphorylamino acid (P-AA) selected from the group consisting of Ser, Thr and Tyr (hereinafter referred to as a "reporter molecule," or "reporter") competes with a phosphorylated substrate molecule, comprising the same P-AA as the reporter molecule, for an antibody specific for the P-AA. The antibody and reporter molecule are chosen so that binding of the antibody, to the reporter causes a change in the reporter which is detectable using FP, FQ, or FCS. Knowledge of the concentration of reporter and substrate used, the dissociation constant ($K_d$) of the phosphorylated substrate for the antibody, the $K_d$ of the reporter for the antibody, and the change in the fluorescent properties of the reporter will allow calculation of the amount of phosphorylated substrate present, and the determination of kinase or phosphatase activity, as is described below.

Thus, by the methods of the invention, phosphorylation of a substrate peptide or protein by a kinase can be monitored by specific displacement of a reporter molecule from an antibody by the reaction product of the kinase assay (the phosphorylated substrate molecule). One assay format for the fluorescent kinase assay is given below.

(1)

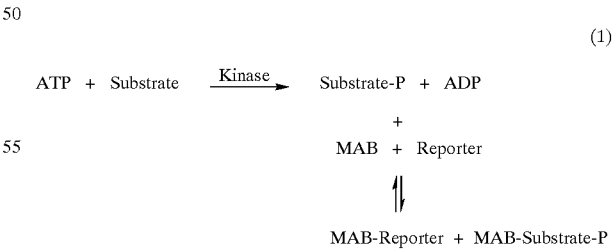

In this new scheme, a kinase reaction is carried out in a reaction mixture by contacting a kinase with a substrate molecule in the presence of a high energy phosphate source such as ATP or GTP. The reaction is allowed to proceed for a period of time, and is stopped (for example, by the addition of a metal chelator such as EDTA or EGTA). Subsequently, both antibody and reporter are added to the reaction mixture, whereby the reaction product (the phosphorylated substrate molecule) specifically displaces the reporter molecule from the antibody.

In another embodiment, the antibody and reporter molecule are present at time=0, so that the phosphorylated substrate competes with the reporter for the antibody, giving intermediate values of polarization and/or quenching, thus providing a homogeneous format for high-throughput screening. Of course, one of ordinary skill will realize that the antibody and reporter molecule can only be present at the time that the enzyme is added where neither the antibody nor the reporter are a substrate for the enzyme.

Thus, the invention provides a method of determining the phosphorylating activity of an enzyme comprising the steps of:
(a) combining said enzyme with
  (i) a reporter molecule comprising a fluorescent label and a phosphorylated amino acid, wherein said amino acid is selected from the group consisting of serine, threonine and tyrosine;
  (ii) a substrate capable of being phosphorylated by said enzyme at the same amino acid which is phosphorylated in said reporter;
  (iii) an anti-phosphorylamino acid antibody which is specific for said phosphorylated amino acid, and which selectively binds to a molecule comprising said phosphorylated amino acid; and
  (iv) a high energy phosphate source
(b) measuring the FP, FQ, or FCS of said reporter following the combination of step (a); and
(c) using the FP, FQ, or FCS measurement of step (b) to determine the activity of said enzyme.

In one embodiment, the substrate is combined with the enzyme before the addition of said reporter and said antibody. In another embodiment, the substrate, the reporter, and the antibody are combined with the enzyme simultaneously.

As described, the dephosphorylation of a substrate peptide or protein can be also be measured by the competitive immunoassays of the present invention. Thus, in another embodiment, the invention provides a method for determining the dephosphorylating activity of an enzyme comprising the steps of:
(a) combining said enzyme with
  (i) a reporter molecule comprising a fluorescent label and a phosphorylated amino acid, wherein said amino acid is selected from the group consisting of serine, threonine and tyrosine;
  (ii) a substrate comprising the same phosphorylated amino acid as said reporter, wherein said substrate is capable of being dephosphorylated at said amino acid by said enzyme; and
  (iii) an antibody which selectively binds to a molecule comprising said phosphorylated amino acid;
(b) measuring the FP, FQ, or FCS of said reporter following the combination of step (a); and
(c) using the FP, FQ, or FCS measurement of step (b) to determine the dephosphorylating activity of the enzyme.

As in the kinase assay described above, the antibody and reporter molecule may be added after the phosphatase reaction has proceeded for some time, in which case the remaining phosphorylated substrate will specifically displace the reporter molecule from the antibody. Alternatively, the antibody and reporter molecule may be present at time=0, so that the phosphorylated substrate competes with the reporter for the antibody, giving intermediate values of polarization and/or quenching. As is true for the kinase assay, the antibody and reporter molecule can only be present at the time that the enzyme is added where neither the antibody nor the reporter are a substrate for the enzyme.

Because the methods of the invention utilize a competitive immunoassay to determine the amount of phosphorylated or dephosphorylated substrate (i.e., the amount of product) produced, the amount of phosphorylated substrate required to displace the reporter from the antibody will vary depending upon the $K_d$ of the phosphorylated substrate for the antibody and the $K_d$ of the antibody for the reporter molecule. Thus, where the $K_d$ of the phosphorylated substrate for the antibody is, e.g., 10-fold less than the $K_d$ of the antibody for the reporter molecule, then an amount of phosphorylated substrate ten times higher than the amount of reporter will be required for the phosphorylated substrate to displace the reporter from the antibody. Where the $K_d$ of the phosphorylated substrate for the antibody is approximately equal to the $K_d$ of the antibody for the reporter molecule, only 50% of the maximal signal can be achieved. In a highly preferred embodiment, the $K_d$ of the phosphorylated substrate for the antibody will be less than the $K_d$ of the antibody for the reporter molecule. In this situation, phosphorylation of the substrate will quantitatively displace the reporter from the antibody.

Another way of reducing the amount of substrate relates to the choice of reporter molecule used in the methods of the invention. A suitable reporter molecule to be used in the methods of the invention is a fluorescently-labeled molecule, preferably a peptide or protein, comprising a phosphorylated amino acid, wherein said amino acid is selected from the group consisting of serine, threonine, and tyrosine. Suitable reporter molecules for use in the methods of the present invention thus include fluorescently labeled phosphoserine, phosphothreonine or phosphotyrosine, as well as an appropriately fluorescently labeled peptide comprising a phosphorylamino acid (P-AA) selected from the group consisting of Ser, Thr and Tyr. Selection of reporter wherein the $K_d$ of the antibody for the reporter is higher that the $K_d$ of the phosphorylated substrate for the antibody will reduce the amount of substrate needed to displace the reporter from the antibody. Because anti-phosphorylamino acid antibodies may have a higher affinity for a fluorescently labeled phosphorylamino acid than for a fluorescently labeled peptide comprising the same phosphorylamino acid, in a preferred embodiment, such peptides are used as the reporter.

Production of peptides to be used as reporters may be accomplished by any one of a number of methods that are well known to those of ordinary skill, such as by enzymatic cleavage, chemical synthesis, or expression of a recombinantly produced peptide. The reporter peptide may be synthesized and then phosphorylated, or instead the phosphorylated amino acid or amino acids may be incorporated into the peptide at the time that the peptide is synthesized. Phosphorylamino acids for incorporation into chemically synthesized peptides may be obtained from numerous commercial sources, such as Sigma (St. Louis, Mo.). In preferred embodiment, labeling of the reporter is accomplished by including a Cys residue in the sequence one to two residues away from the phosphorylatable amino acid.

Suitable fluorescent labels to be used in the methods of the invention include any fluorophore that, upon the binding of the reporter molecule by an anti-phosphorylamino acid antibody, undergoes a change detectable by FP, FQ, or FCS. Of course, in order to be used in the methods of the invention, the label cannot interfere with recognition of the reporter by the anti-phosphorylamino acid antibody. Where the detection method to be used is FP, the fluorescent label to be used may be any probe which, when combined with a molecule comprising a phosphorylated amino acid (P-AA) selected from the group consisting of Ser, Thr and Tyr to form a reporter molecule, undergoes a change in fluorescence lifetime when the reporter molecule binds to a larger molecule (i.e., the antibody). Where the detection method to be used is FQ, the fluorescent label to be used may be any environment-sensitive probe which, when combined with a molecule comprising a phosphorylamino acid (P-AA) selected from the group consisting of Ser, Thr and Tyr to form a reporter molecule, undergoes a change in fluorescence intensity when the reporter molecule binds to a larger molecule (i.e., the antibody). In FCS, the difference in the diffusion coefficients of two bound molecules (with the smaller of the two being fluorescently labeled) is observed in a very small volume. Thus, the smaller, labeled molecule will diffuse into the observed volume faster in the unbound state than it will if bound to a larger molecule. For this technique, any probe that undergoes minimal photobleaching can be used, with preference given to those with the highest quantum yields.

Utilization of a FRET assay format results in a continuous recording assay for either phosphatase or kinase activities. Where a FRET format is to be used, the antibody is labeled with a suitable donor or acceptor fluorophore, while the substrate is labeled with the donor or acceptor fluorophore that complements the fluorophore labeling the antibody. For example, the substrate peptide can be labeled with a donor fluorophore such as fluorescein or Oregon green, while the antibody is labeled with a suitable fluorophore acceptor, such as rhodamine, with excitation at the absorbance maximum of the donor, and emission observed at the maximum of either fluorophore. Thus, as the target amino acid of the labeled substrate becomes phosphorylated, the labeled antibody will bind to the substrate, resulting in both the quenching of the donor fluorescence and the enhancement of the acceptor fluorescence.

An antibody suitable for use in the FP, FQ, FRET and FCS methods of the invention is one that binds specifically to phosphoserine, phosphothreonine, or phosphotyrosine, and that produces changes in either the intrinsic polarization or quenching of the emission intensity of the fluorosceinated version of the phosphorylamino acid to which it binds. Furthermore, where the assay format used is FP, FQ, or FCS, the difference between the $K_d$ of the antibody for the phosphorylated substrate and the $K_d$ of the antibody for the reporter molecule will dictate the amount of phosphorylated substrate that must be present in order for the phosphorylated substrate to displace the reporter from the antibody. Thus, where the $K_d$ of the phosphorylated substrate for the antibody is, e.g., 10-fold less than the $K_d$ of the antibody for the reporter molecule, then an amount of phosphorylated substrate ten times higher than the amount of reporter will be required for the phosphorylated substrate to displace the reporter from the antibody. Where the $K_d$ of the phosphorylated substrate for the antibody is approximately equal to the $K_d$ of the antibody for the reporter molecule, only 50% of the maximal signal can be achieved. In a highly preferred embodiment, the $K_d$ of the phosphorylated substrate for the antibody will be less than the $K_d$ of the antibody for the reporter molecule. In this situation, phosphorylation of the substrate will quantitatively displace the reporter from the antibody.

Because the methods of the invention are to be used to assay kinase and phosphatase activity, it is preferred that displacement of the reporter molecule from the antibody be accomplished with a relatively low concentration of phosphorylated substrate. As is described above, this may be accomplished by using a reporter having a $K_d$ for the antibody that is higher than the $K_d$ of the phosphorylated substrate for the antibody, and will allow detection of lower concentrations of phosphorylated substrate. With proper selection of the reporter, the assay format can be FP, FQ, or FCS.

Anti-phosphorylamino acid antibodies may be obtained from numerous commercial sources, including Sigma (St. Louis, Mo.), ICN Biomedicals (Costa Mesa, Calif.), Life Technologies (Gaithersburg, Md.), Transduction Labs, (Lexington, Ky.), Molecular Biology Laboratories (Nagoya, Japan), Upstate Biologicals (Lake Placid, N.Y.) and Zymed Laboratories (South San Francisco, Calif.). In addition, anti-phosphorylamino acid antibodies may be prepared as described in Zoppini et al. (*Eur. J. Lab. Med.* 1(2):101–103 (1993)), and in the references cited therein. Determination of whether a certain anti-P-AA antibody produces changes in either the intrinsic polarization or quenching of the emission intensity of the F-P-AA may be made according to the method described in Example 1.

As used herein, the term "antibody" includes monoclonal antibodies, polyclonal antibodies, single chain antibodies, and ligand-binding fragments of antibodies, such as Fab and F(ab')$_2$. Various procedures known in the art may be used to produce such antibodies and fragments. For preparation of monoclonal antibodies, any technique which provides antibodies produced by continuous cell line cultures may be used, such as the hybridoma technique of Kohler and Milstein (*Nature*, 256:495–497 (1975)). Techniques for the production of single-chain antibodies (U.S. Pat. No. 4,946,778) can be adapted to produce single chain antibodies to phosphoserine, phosphothreonine, or phosphotyrosine.

As may be seen from the above discussion, the assay format gives the user a great deal of latitude for tailoring reagents and reaction conditions to meet the requirements of a specific kinase or phosphatase.

Changes in the fluorescent properties of the reporter may be measured using any technique capable of detecting a change in the fluorescent properties of a molecule. Such methods include, but are not limited to, fluorescence polarization, fluorescence quenching, fluorescence resonance energy transfer, and fluorescence correlation spectroscopy.

Fluorescence polarization: Fluorescence polarization (FP), in contrast to intensity measurements, can readily be used in the development of true, homogeneous, solution assays, or for real time, continuous recording assays, as the method can generate a direct quantitation of the ratio of bound/free ligand. This is extremely cost effective in terms of simplicity of operations and the types of screening laboratory ware required for the assay. Since polarization is independent of the fluorescence intensity, this technique can be used in the presence of colored compounds which may quench the emission.

When a fluorescent molecule is excited by polarized light, its emission is also polarized. The degree of polarization is dependent upon the viscosity of the solution, the rotational correlation time of the fluorophore ($\phi$), and the temperature of the reaction mixture. Mathematically, the steady-state polarization (P) is expressed as $$P = \frac{I_\parallel - I_\perp}{I_\parallel + I_\perp} \quad (2)$$

which is the difference between the intensities (I) of the parallel and perpendicular components of the polarized emission divided by their sum. More recently, the fluorescence anisotropy (r), which is dependent on the extent of rotational motion during the lifetime of the excited state, is being used because theoretical expressions are simpler when expressed in terms of this parameter rather than P. P is related to r by the expression $$P = \frac{3r}{2+r}. \quad (3)$$

Since P, unlike r, is not completely linear with fraction bound, it is more beneficial to use r for the calculations, especially if the quantum yields of the free ($q_F$) and bound ($q_B$) species are not equal. The corrected fraction bound in this case is given by $$FB = \frac{r - r_F}{(r_B - r)R + r - r_F} \quad (4)$$

where $r_F$ and $r_B$ are the anisotropies of the totally free and totally bound species respectively, r is the anisotropy of the experimentally observed bound species, and $R = q_B/q_F$. Titration of the fluorescent component with the nonfluorescent component yields data which is readily analyzable by various forms of the Langmuir binding isotherm or the stoichiometric binding equation if the binding is specific.

The requirements for a polarization assay are: (1) an assay component (the one with the lowest molecular weight) must be labelled with a long lifetime fluorescent probe and retain its ability to bind to the other component(s), (2) there must be a sufficient difference between the molecular weight of the labelled component and the nonlabeled one such that the probe senses a significant volume change upon binding, (3) the probe must have a relatively high quantum yield so that its fluorescence at low concentrations is significantly greater than background (4) the temperature and viscosity of the reaction mixture must be strictly controlled, and (5) the polarization should increase in a dose-dependent saturable manner. For use in plate-reader format, the fluorophore used should be a bright visible probe such as, e.g., fluorescein or rhodamine. Thus, where the detection method to be used is fluorescence polarization, the fluorescent label to be used may be any environment-sensitive probe whose fluorescence lifetime changes upon binding to a larger molecule.

The changes observed in the anisotropy free and bound ligands are a function of their individual rotational correlation times. Thus, in order to obtain a good dynamic range for the assay, the rotational correlation time of the labeled antigen should be shorter than the lifetime of the fluorescent tag. Since most visible probes have lifetimes $\leq 10$ ns, the polarization assay is limited generally to the binding of small labelled ligands to large unlabelled targets. Thus it is generally not possible to study by polarization methods the interaction of two large macromolecules.

Fluorescence Quenching: HTS assays that utilize the intensity of the fluorophore as a readout usually require the separation of the free and bound species unless an environment-sensitive fluorophore is utilized. However, there are very few probes of this nature which both absorb and emit in the visible range, and as such, are not useful for HTS. In some cases, however, binding of the nonfluorescent component to the labelled ligand may result in a concentration-dependent quenching or enhancement of the fluorescence which may occur due to the presence of quenching groups in the unlabelled component or some chemistry of the binding site which affects the fluorescence emission of the fluorophore. Thus the concentration-dependent decrease (or increase) in the fluorescence emission may be used to quantitate binding. The advantage of this readout is that a simple fluorescence plate reader may be used without polarizers. The usefulness of this assay may be limited where colored compounds which also quench the fluorophore are present in the assay mixture. Thus, where the detection method to be used is fluorescence quenching, the fluorescent label to be used may be any environment-sensitive probe whose fluorescence intensity changes upon binding to a larger molecule.

Fluorescence Resonance Energy Transfer: Fluorescence resonance energy transfer (FRET) is the transfer of the excited state energy from a donor (D) to an acceptor (A), and occurs only when the emission spectrum of the donor (D) fluorophore overlaps the absorption spectrum of the acceptor (A) fluorophore. Thus, by exciting at the absorption maximum of the donor and monitoring the emission at the long wavelength side of the acceptor fluorophore, it is possible to monitor only D and A molecules that are bound and reside within a certain distance, r. Thus one can monitor either the quenching of D or enhanced emission of A. The transfer rate, $k_T$ in $sec^{-1}$ is mathematically defined as $$k_T = (r^{-6} J \kappa^2 n^{-4} \lambda_d) \times 8.71 \times 10^{23} \quad (5)$$

where r is the D-A distance in angstroms, J is the D-A overlap integral, $\kappa^2$ is the orientation factor, n is the refractive index of the media, and $\lambda_d$ is the emissive rate of the donor. The overlap integral, J, is expressed on the wavelength scale by $$J = \int_0^\infty F_d(\lambda) \epsilon_a(\lambda) \lambda^4 \, d\lambda \quad (6)$$

where its units are $M^{-1}cm^3$, $F_d$ is the corrected fluorescence intensity of the donor as a function of wavelength $\lambda$, and $\epsilon_a$ is the extinction coefficient of the acceptor in $M^{-1}cm^{-1}$.

Constant terms in equation 4 are generally combined to define the Forster critical distance, $R_o$, which is the distance in angstroms at which 50% transfer occurs. By substitution then, $R_o$ can be defined in terms of the overlap integral, J, in angstroms, as $$R_o = 9.79 \times 10^3 (\kappa^2 n^{-4} \phi_d J)^{1/6} \quad (7)$$

with $\phi_d$ being the quantum yield of the donor.

$R_o$ and r are related to the transfer efficiency, E, by $$E = \frac{R_o^6}{R_o^6 + r^6} \quad (8)$$

which determines the practical distance by which D and A can be separated to obtain a usable signal.

From these equations it is easy to see that, for high sensitivity, it is important to choose D-A pairs which have high quantum yields, high J values, and high $R_o$ values. For example, $R_o$ for the fluorescein/rhodamine pair is about 55 Å. Large values of $R_o$ are necessary to achieve a measurable signal when molecules containing D and A bind to each other. In practice it is common to use twice as many acceptor as donor molecules in the reaction mixture if the emission of A is to be used as the readout. Thus, binding of, for example, macromolecule I labelled with D, to macromolecule II labelled with A, can be detected by the emission of A when excited at the absorption of D. Again, for a competitive process, the concentration increase in A fluorescence must occur in a hyperbolic, saturable manner. The FRET assay is thus especially desirable for monitoring the binding of two large macromolecules where FP techniques are not particularly useful.

In view of the guidelines provided above and in the Examples, below, the skilled practitioner will be able to choose the detection technique best suited for the particular assay being performed.

Having generally described the invention, the same will be more readily understood by reference to the following examples, which are provided by way of illustration and are not intended as limiting.

EXAMPLES

Example 1

Materials and Methods (a) Reagents: Antibodies to phosphoryltyrosine were obtained from ICN Biomedicals, Inc., Costa Mesa, Calif., (monoclonal antibody clone PY20, Catalog Number 69-137), Life Technologies, Gaithersberg, Md., (monoclonal antibody clone 6G9, Catalog Number 13160–011), Molecular Biology Laboratories, Nagoya, Japan (monoclonal antibody clone 6D12; Catalog Number MH-11-3), Sigma, St. Louis Mo., (monoclonal antibody clone PT-66, Catalog Number B-1531), Transduction Labs, Lexington, Ky. (monoclonal antibody clone PY20, Catalog Number P11120; altered Fab of PY20 produced in *E. coli*, Catalog Number E120H), Upstate Biologicals Inc., Lake Placid N.Y., (monoclonal antibody clone 4G10, Catalog Number 05-321), and Zymed Laboratories, Inc., South San Francisco, Calif., (monoclonal antibodies, clone PY-7E1, Catalog Number 13-5900; clone PY-IB2, Catalog Number 13-6300; clone PY20, Catalog Number 03-7700; clone Z027, Catalog Number 03-5800; and polyclonal antibodies Catalog Number 61-5800 and 61-8300).

Antibodies to phosphorylthreonine were obtained from Sigma (monoclonal antibody clone PTR-8, Catalog Number B-7661) and Zymed (monoclonal antibody, clone PT-5H5, Catalog Number 13-9200; polyclonal antibody, Catalog Number 61-8200). Antibodies to phosphorylserine were obtained from Sigma (monoclonal antibody clone PSR-45, Catalog Number B-7911) and Zymed (polyclonal antibody, Catalog Number 61-8100). The structures of all chemicals used are shown in FIG. 1.

(b) Synthesis of amino-fluorescinated phosphorylamino acids: The amino-fluoresceinated, phosphorylamino acids (i.e.—serine, threonine and tyrosine) were synthesized by reacting the phosphorylamino acids with fluorescein isothiocyanate (FITC) (Pierce Chemical Company) in 0.1 M $NaHCO_3$ of pH 9. The FITC used was a mixture of the two isomers shown in FIG. 1. Purification was performed using a C4 Reverse Phase column (2.5 mm×25 cm), a flow-rate of 0.5 ml/min, and a 15 minute gradient from 0.01 N HCl to 100% $CH_3CN$. The fluoresceinated phosphorylamino acids were identified by mass spectral analysis. For these compounds, a molar extinction coefficient of 77,000 was assumed in pH 8 buffer with a 1 cm pathlength.

(c) Fluorescence Measurements: Ratiometric fluorescence measurements were made using an ISS K2 spectrofluorometer equipped with Glans Thompson quartz polarizers. The temperature of the reaction cuvette was maintained at 25.0° C. by a Lauda RM6 circulating bath. The fluorescence of the labelled phoshorylamino acids was measured with excitation at 485 nm and emission was observed through an Omega 530±15 nm bandpass filter.

Antibody binding to the fluoresceinated phosphorylamino acids was monitored by adding successive small volumes of the antibody stock solution to a cuvette containing a fixed amount of fluoresceinated phosphorylamino acid in two milliliters of pH 7.4 buffer (25 mM Tris and 25 mM NaCl adjusted to pH 7.4 with HCl). The fluorescence polarization, anisotropy, and the intensity—the sum of vertically and horizontally polarized emissions—were recorded one minute after each addition. The dilution produced by the addition of the antibody necessitated a slight correction for both the concentrations and the intensity readings but not for the polarization since the latter is independent of the fluorophore concentration. Displacement of the fluorophore from the antibody by competing nonfluorescent ligands was measured by using fixed amounts of antibody and fluorophore in two milliliters of pH 7.4 buffer and adding successive small volumes of the competitor stock solution. Again, the displacement was monitored one minute after each addition by the changes in fluorescence intensity, polarization, and anisotropy Data Analysis: Data analysis was performed as follows. It is assumed that the binding of the fluorophore ligand, L, and the competing inhibitor, I, to the antibody, A, are rapid, simple thermodynamic equilibria, according to the scheme:

$$L + A \xrightleftharpoons{K_l} C \tag{1}$$

$$I + A \xrightleftharpoons{K_i} X \tag{2}$$

with $K_l = L \cdot A/C$ and $K_i = I \cdot A/X$.

Case I: Displacement with $A_o \gg L_o$: For the displacement experiments—where both $L_o$ and $A_o$ are constant and $I_o$ increases—the analysis of the data is greatly simplified when it is possible to use experimental conditions where $I_o \gg A_o$ and $A_o \gg L_o$. Under these conditions, $L = L_o - C$; $I = I_o$; $X = A \cdot I_o/K_i$; $A_o = A + X$ $A(1 + I_o/K_i)$. Therefore $A = A_o/(1 + I_o/K_i)$ and $$K_1 = \frac{(L_o - C)A_o}{C \cdot \left(1 + \frac{I_o}{K_i}\right)} \tag{3}$$

Upon solving (3) for C we obtain:

$$C = \frac{C_u}{1 + \frac{I_o}{K_i^{app}}}. \tag{4}$$

in which we define the concentration of the fluorophore/antibody complex in the absence of inhibitor as $C_u = L_o/(1 + K_l/A_o)$ and the apparent inhibition constant as $K_i^{app} = K_i \cdot (1 + A_o/K_l)$. In these experiments one can directly determine only $K_i^{app}$. The value of $K_i$ can be calculated only if $L_o$ and $K_l$ are known.

Case IIa: Binding: The analysis of the direct binding of a constant concentration of fluorophore, $L_o$, to a variable concentration of antibody, $A_o$, of comparable magnitude requires solving a quadratic equation. By substituting L and A from the stoichiometric equations $L_o = L + C$ and $A_o = A + C$ into the definition of $K_l$ we obtain:

$$K_1 = \frac{(L_o - C) \cdot (A_o - C)}{C} \quad (5)$$

which yields the quadratic equation:

$$C^2 - C \cdot (A_o + L_o + K_1) + L_o A_o = 0 \quad (6)$$

The solution of (6) is $$C = \frac{1}{2} \cdot \left(A_o + L_o + K_1 - \sqrt{(A_o + L_o + K_1)^2 - 4 \cdot A_o \cdot L_o}\right) \quad (7)$$

Case IIb: Displacement: The usual conditions for the displacement experiments are $L_o$ and $A_o$ constant but of comparable magnitude with increasing $I_o$ and $I_o \gg A_o$. Under these conditions, $L = L_o - C$; $I = I_o$; and $X = A \cdot I_o/K_i$. Therefore $A_o = A + C + X = C + A \cdot (1I_o/K_i)$ so that $$A = \frac{A_o - C}{1 + \frac{I_o}{K_i}} \quad (8)$$

and $$K_1 C = L \cdot A = \frac{(L_o - C) \cdot (A_o - C)}{1 + \frac{I_o}{K_i}} \quad (9)$$

Solving (9) for $C$ yields $$C = \frac{1}{2} \cdot \left(A_o + L_o + K_1 \cdot \left(1 + \frac{I_o}{K_i}\right) - \sqrt{\left[A_o + L_o + K_1 \cdot \left(1 + \frac{I_o}{K_i}\right)\right]^2 - 4 \cdot A_o \cdot L_o}\right) \quad (10)$$

Fluorescence Intensity: The fluorescence intensity, F, of a mixture of L and C is $$F = Q_L \cdot L + Q_C \cdot C = Q_L \cdot L_o + (Q_L - Q_C) \cdot C \quad (11)$$

where $Q_L$ is the molar emissivity of the free fluorophore and $Q_C$ that of the bound one. Substituting into this equation C from Eq 7 yields the quadratic used to analyze the fluorescence intensity binding data obtained under Case IIa.

Similarly, substituting the expression for C from Eq 4 or from Eq 10 yields the expression for analyzing the fluorescence displacement data under Cases I or IIb, respectively.

Fluorescence Polarization and Anisotropy: The analysis of the changes in fluorescence intensity upon binding to the antibody are relatively simple because the changes are a linear function of the composition of the L+C mixture. As pointed out previously (7), this is not the case in general when changes in fluorescence polarization or anisotropy are measured. Indeed, if the exciting electric vector is vertical, then the polarization of a solution is a function of the emitted intensities horizontally polarized, h, and vertically polarized, v, according to the definition:

$$p = \frac{v - h}{v + h} \quad (12)$$

The total fluorescence intensity is $F = h + v = Q \cdot M$, where Q is the molar emissivity of the fluorophore at concentration M. Solving Eq 12 for v yields $v = h \cdot (1+p)/(1-p)$. Thus:

$$Q \cdot M = h \cdot \left(1 + \frac{1 + p}{1 - p}\right) \quad (13)$$

and it follows that $$h = \frac{Q \cdot M (1 - p)}{2} \quad (14)$$

with $$v = \frac{Q \cdot M (1 + p)}{2} \quad (15)$$

For a mixture of L and C, the polarizations calculated from the sum of the vertically and horizontally polarized emission intensities are:

$$p = \frac{v_L + v_C - h_L - h_C}{v_L + v_C + h_L + h_C} \quad (16)$$

Substituting $h_L = Q_L L(1-p_L)/2$, $h_C = Q_C C(1-p_C)/2$, $v_L = Q_L L(1+p_L)/2$, and $v_C = Q_C C(1+p_C)/2$, where $p_C$ and $p_L$ are the polarization values for the bound ligand and the free ligand, respectively, and then solving for C/L yields, as reported earlier (7):

$$\frac{C}{L} = \frac{C}{L_o - C} = \frac{Q_L}{Q_C} \frac{p - p_L}{p_C - p} \quad (17)$$

Similarly, from the definition of the fluorescence anisotropy, $a$,:

$$a = \frac{v - h}{v + 2h} \quad (18)$$

we derive:

$$\frac{C}{L} = \frac{C}{L_o - C} = \frac{Q_L}{Q_C} \frac{2 + a_C}{2 + a_L} \frac{a - a_L}{a_C - a} \quad (19)$$

where $a_C$ and $a_L$ are the fluorescence anisotropies for the bound ligand and the free ligand, respectively.
Eq 17 can be solved for p as a function of C:

$$p = \frac{p_L L_o + C \left[\frac{Q_C}{Q_L} p_C - p_L\right]}{L_o + C \left[\frac{Q_C}{Q_L} - 1\right]} \quad (20)$$

Of course, when the molar emissivity does not change upon binding, i.e. when $Q_C/Q_L = 1$, then p becomes a linear function of C, in full analogy with the fluorescence intensity as expressed in Eq 11.

When $Q_C/Q_L \neq 1$ then substituting into Eq 20 the value of C from the appropriate equation (Eq 4, Eq 7, or Eq 10) allows one to determine $K_I$ and $K^{app}_i$ or $K_i$ by nonlinear least squares analysis of the polarization data. Depending on the experimental conditions used, such an analysis may also yield the best-fit values for $p_L$, $p_C$, $Q_L$, and $Q_C$.

Results

The majority of the anti-phosphorylamino acid antibodies available from suppliers were evaluated, looking for those that produced changes in either the intrinsic polarization or quenching of the emission intensity of the fluoresceinated phosphorylamino acids. From the results of this survey, three classes of antibodies were identified for phosphoryltyrosine, based on the types of fluorescent signal produced by the antibody: (I) those giving a large polarization change without significant effect on the fluorescence emission of the fluorescent phosphorylamino acid, (II) those producing polarization changes and quenching of the emission, and (III) those yielding little or no change in either parameter, or produced noisy, nonreproducible data.

Due to sensitivity considerations, titrations of the fluorescent phosphorylamino acids with the antibodies were performed at comparable concentrations of $A_o$ and $L_o$. Under these conditions, one must use the quadratic form of the binding equation (Equation 7) in order to determine with precision the $K_d$ of the ligand for the antibody and the stoichiometry of the reaction. The concentration of $L_o$ was calculated from the extinction coefficient of the fluorophore. However, the concentration of the stock solution of the antibody is given in units of protein concentration/ml, not active antibody which has two binding sites/molecule.

The antibody concentrations were first calculated using the protein concentrations supplied by the manufacturer, assuming a molecular weight of 160,000. [1]. Calculations done in this manner do not take into consideration the bidentate nature of the antibody. Thus, the site-concentration or normality of the antibody should be twice the concentration calculated as described above. Calculation of antibody concentrations based on protein quantitation would exceed the actual antibody concentration, due to the presence of extraneous contaminating proteins and/or inactive antibody. For these reasons, in the titration curves, antibody concentrations are given in terms of the volume of antibody added, and the actual $K_d$s of the fluorescent phosphorylamino acids are calculated from the fitted stoichiometry, which has concentration units of molar sites (i.e., normality). Comparison of the determined stoichiometry with concentrations calculated from protein concentrations can then be used to assess the purity and activity of antibodies from different manufacturers.

Examples of experimental results using Type I antibodies (as described above) are shown in FIG. 2. Addition of any of the Sigma anti-phosphorylamino acid antibodies to the corresponding fluoresceinated phosphorylamino acid produced a steep, concentration-dependent increase in the polarization of the fluorescence which was saturable at higher antibody concentrations. The maximal increase in polarization at saturating antibody concentrations was approximately 9-fold for antibody binding to labelled (i.e.—fluoresceinated) phosphorylamino acids with an excellent signal-to-noise ratio. The Sigma antibodies are thus Type I antibodies (FP change only). The data sets were analyzed using Equation 7 in conjunction with a nonlinear least squares fitting program and are consistent with this model as evidenced by the agreement between the experimental data points and the theoretical curves. The dissociation constant for all the Sigma antibodies, calculated from the fits to the experimental data, are given in Table 1 in units of antibody normality. All three fluoresceinated phosphorylamino acids had a high picomolar to low nanomolar affinities for their corresponding antibodies.

The antibodies were then individually evaluated for their cross-reactivity with the opposite fluoresceinated phosphorylamino acids, and the non-phosphorylated amino acids themselves by competitive displacement immunoassay. None of the antibodies were found to cross react with the other phosphorylamino or amino acids at levels 10–20 fold above those used in the titration experiments. The data for the anti-phosphoserine and anti-phosphothreonine antibodies are discussed more extensively below.

Three anti-phosphotyrosine antibodies which gave both significant increases in the fluorescence polarization and decreases in the emission intensity when bound to P-Tyr-F were also identified (Type II antibodies). Two antibodies, from ICN and MBL, produced the largest decreases in the fluorescence of P-Tyr-F upon binding (Table 1; as $Q_f/Q_b$ increases so does the dynamic range).

Figure 3A:
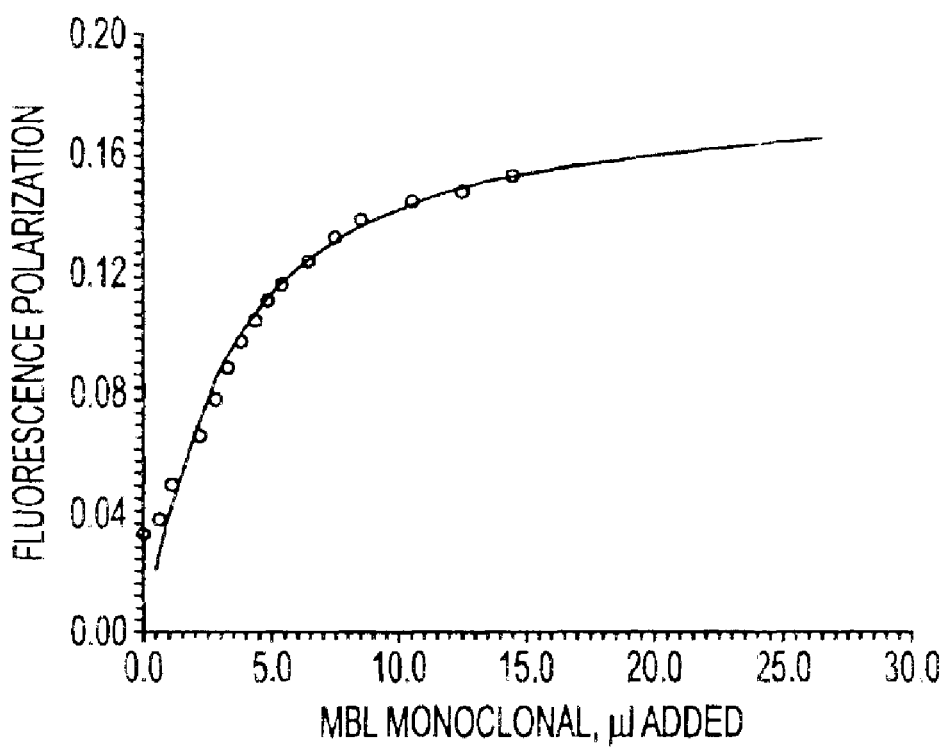
FIGS. 3A and 3B.
Figure 3B:
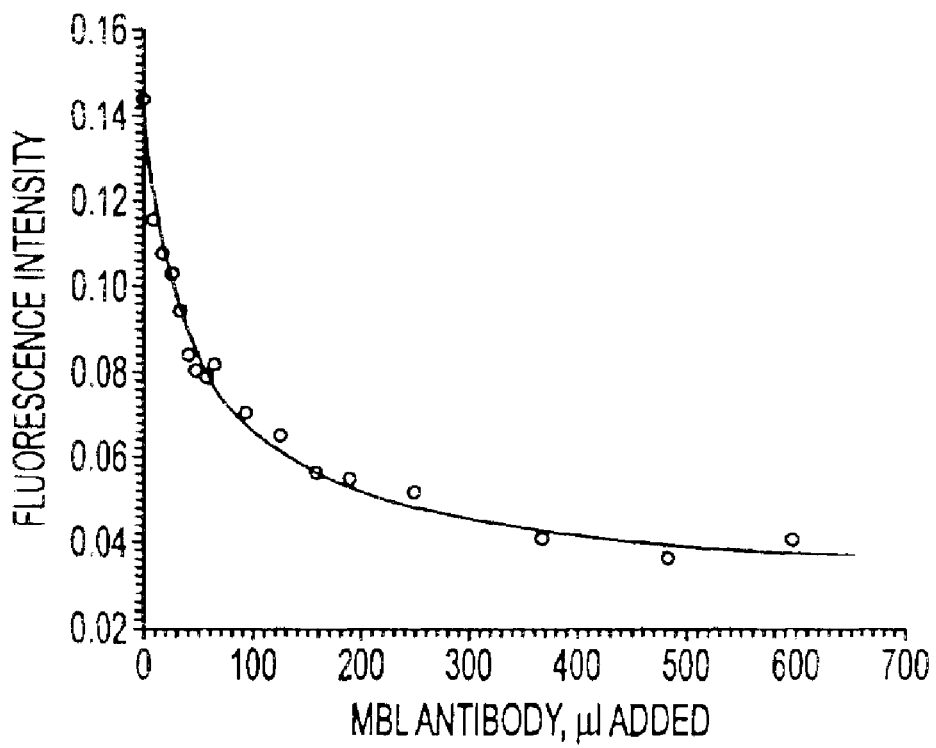
Figure 4A:
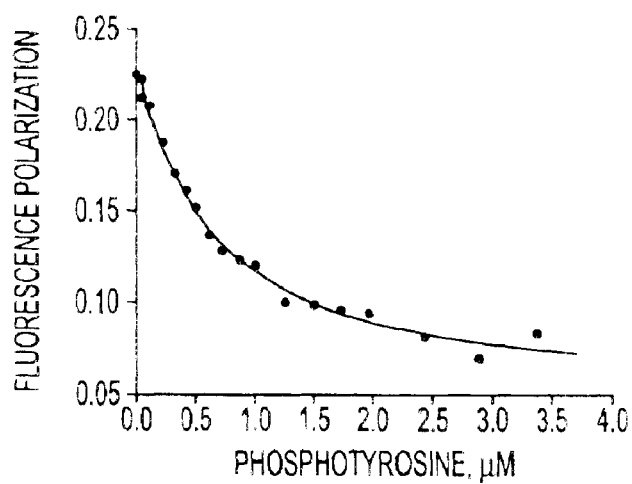
FIGS. 4A, 4B and 4C.
Figure 4B:
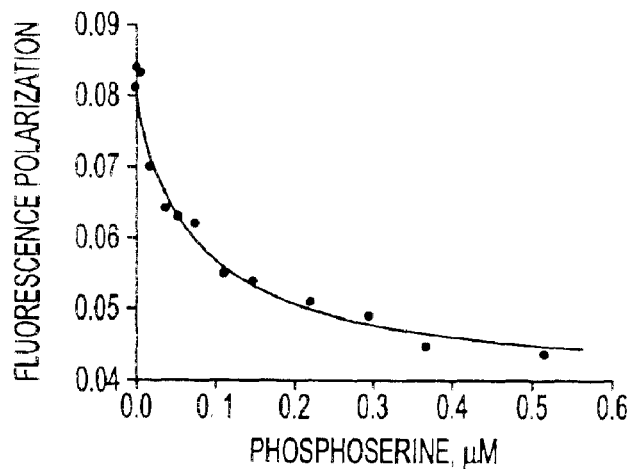
Figure 4C:
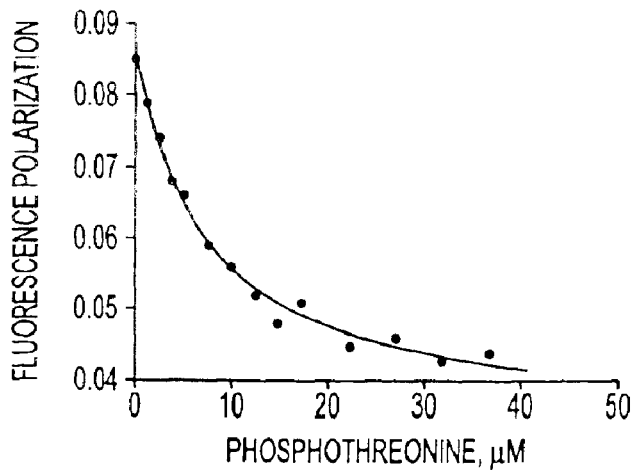
Figure 5A:
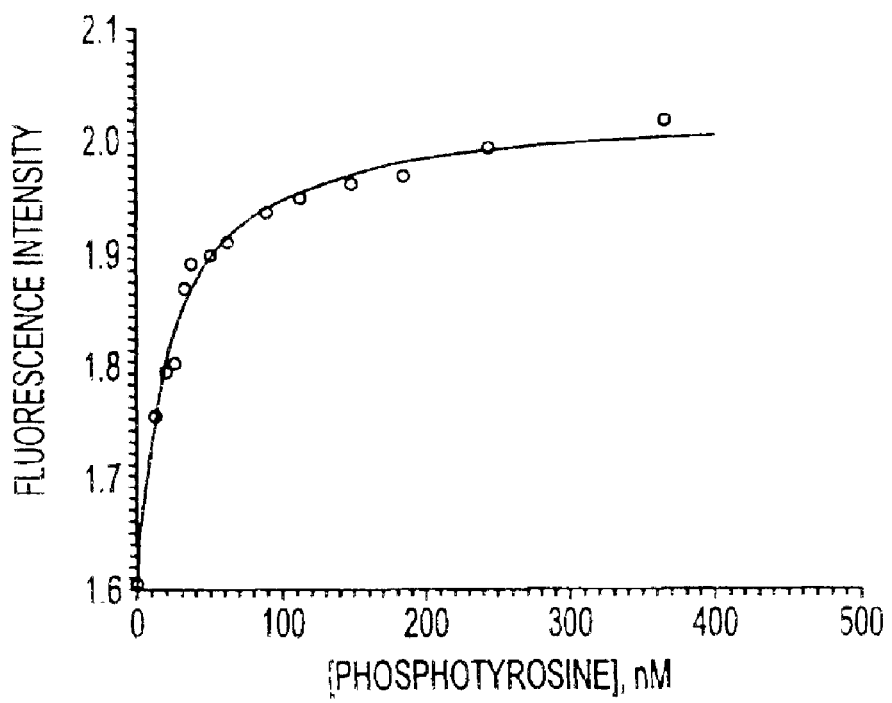
FIGS. 5A and 5B.
Figure 5B:
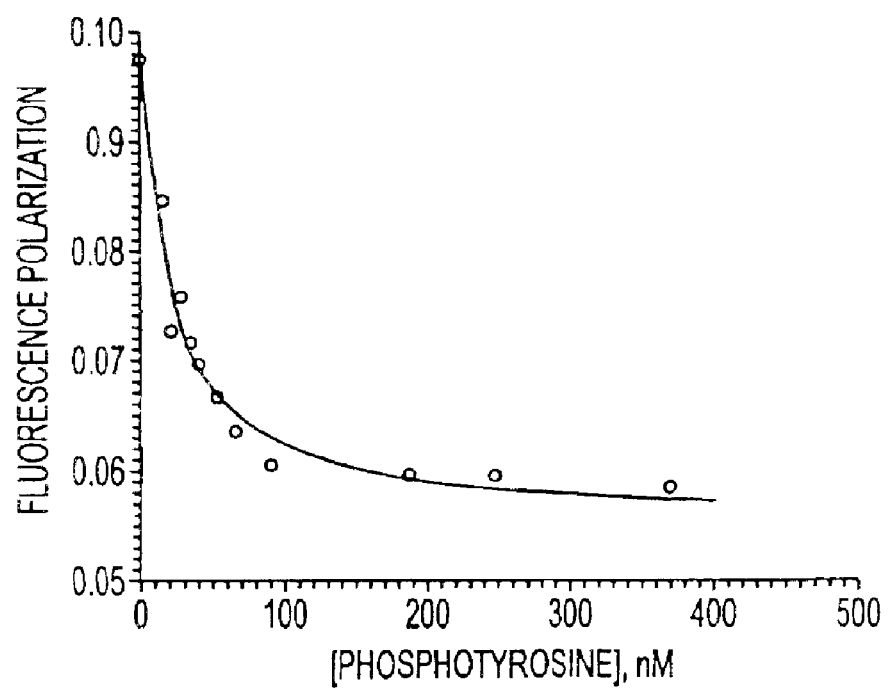
Figure 7A:
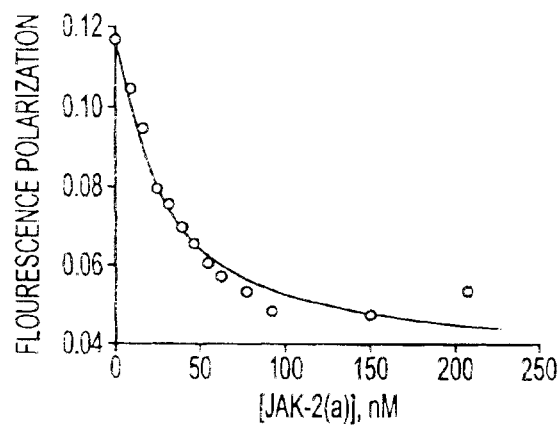
FIGS. 7A, 7B, 7C, and 7D.
Figure 7B:
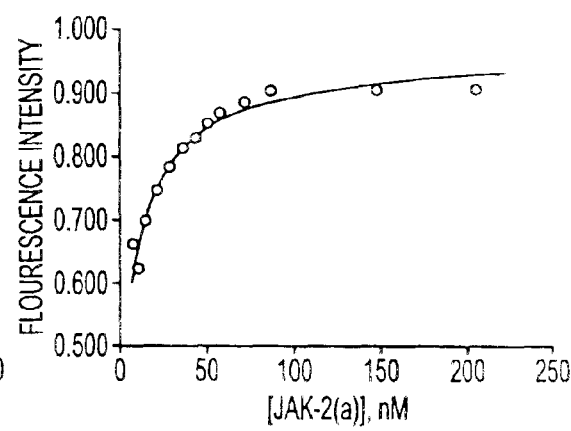
Figure 7C:
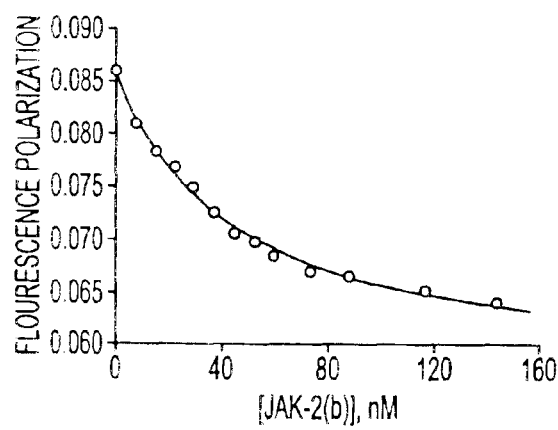
Figure 7D:
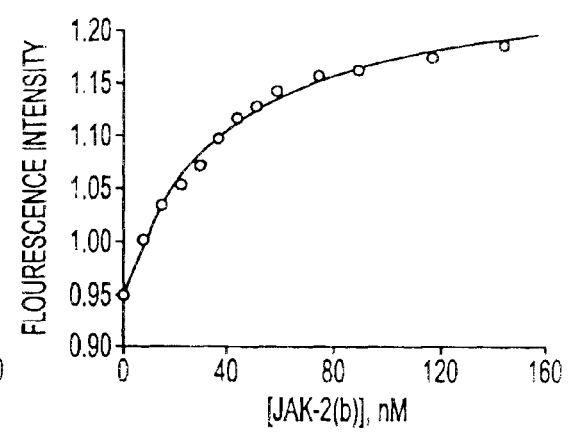

Analysis of the data in FIGS. 3 and 4 using Equations 7 and 20 resulted in fits that were consistent with the experimental points, and there was good agreement between the $K_d$s (low nM) calculated from both the polarization and the intensity readings. Thus, kinase and phosphatase assays utilizing the ICN or MBL antibodies may be performed using either the fluorescence polarization increase or emission quenching as a measure of antibody binding to labeled phosphorylamino acids in the presence of unlabeled phosphorylated reaction products. The cause of the emission quenching by the ICN and MBL antibodies may involve hydrogen bonding of the fluorescent ligand, the presence of tryptophan residues in or near the binding site, or electrostatic interactions.

Other antibodies were found to produce small, nonrobust fluorescence changes upon binding labelled ligand (Table 1), and were considered not to be useful for the kinase assays. Still other antibodies tested produced insignificant or inconsistent changes in either the emission intensity or polarization, and were deemed not usable for either kinase or phosphatase activity detection (Type III antibodies). Interestingly, the superior antibodies (those that gave the most robust signals with the least scatter) had normalities calculated from the fits to the quadratic equation that were in good agreement with concentrations supplied by the manufacturer. In contrast, for the less robust antibodies, there was a great disparity between the stoichiometry and protein concentration calculations, indicating the presence of either contaminating proteins and/or inactive antibody.

Figure 2B:
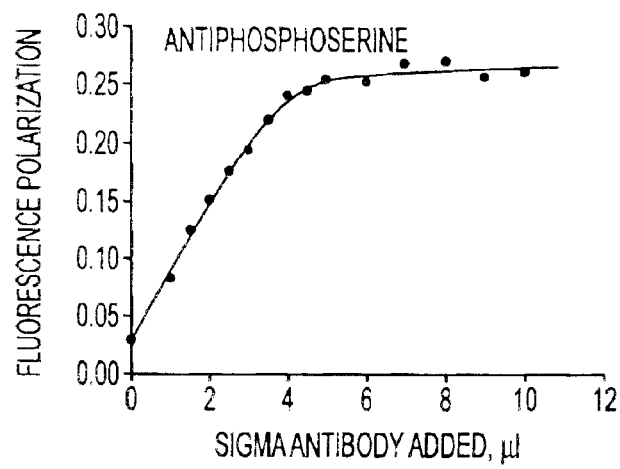
Figure 2C:
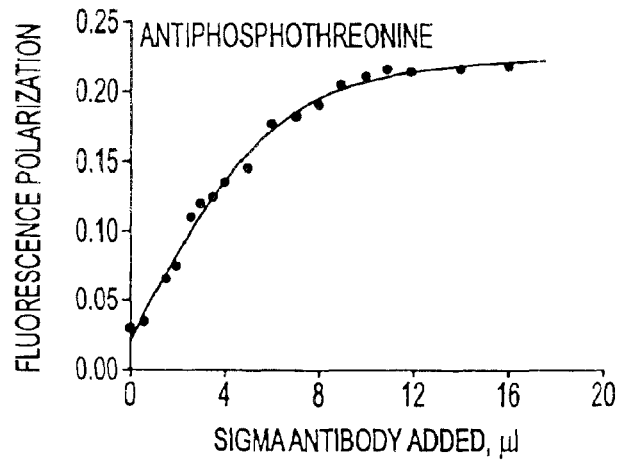

Antibodies for phosphoserine and phosphothreonine came from two sources, Sigma (St. Louis, Mo.) and Zymed (CA). Only the Sigma antibodies were found to produce a signal of significant magnitude that would allow, for kinase and phosphatase assays, accurate quantitation of unlabelled phosphoserine and phosphothreonine (Table 2). The results from experiments with the Sigma antibodies were calculated by nonlinear least squares analysis using equation 7, are shown in FIG. 2. None of the Sigma antibodies produced quenching of the emission intensities, but both P-Ser-F and P-Thr-F had high affinity for their respective antibodies as measured by FP. Although binding of the fluorescent ligands to the Zymed antibodies gave both polarization and intensity changes, they were accompanied by significant scatter and a less than desirable dynamic range to be useful for monitoring either kinase or phosphatase activity.

In order to determine if kinase reactions can be followed by competition of the phosphorylated substrate with labelled phosphorylamino acid, the specificity of the binding by the labeled phoshorylamino acids was demonstrated by co-competition with their unlabeled counterparts for the antibody-bound fluorescent complex. The competition between the labeled and unlabeled phosphorylamino acids for the antibodies was first determined. The amounts of antibody and fluorescent phosphorylamino acid were held constant (close to the $K_d$) in these experiments, and the decrease in polarization or increase in emission resulting from the addition of the unlabelled phosphorylamino acid was monitored as a function of its concentration. The experimental data were analyzed by fixing the concentrations of L, $K_f$, and $Q_L$ using Equation 10 in conjunction with Equation 20 (when polarization with a quenching antibody was measured), or Equation 10 only when the increased polarization was not accompanied by quenching. The results of these experiments are shown in FIGS. 4 (Sigma antibodies) and 5 (MBL antibody). Fitting in the manner described above yielded excellent fits to the experimental data. The values for the corrected dissociation constants of the phosphorylamino acids are given in Table 3. The $K_i$s for phosphoryltyrosine, phosphorylserine, and phosphorylthreonine were considerably higher than those for the fluoresceinated ligands. Good agreement between $K_i$s calculated from the polarization and quenching data were determined for the MBL antibody. These experiments show that kinase and phosphatase activities can be measured with precision using either FP or quenching data.

In order to calculate, by competition with labeled ligand, the amount of phosphorylated or dephosphorylated substrates produced during the course of the kinase or phosphatase reactions, it is imperative to know the dissociation constant of the phosphorylated substrate for the particular antibody. The affinities of two phosphorylated peptides which are substrates for the JAK-2 tyrosine kinase were measured by displacement of fluoresceinated phosphoryltyrosine from both the corresponding Sigma and MBL antibodies. The structure of the first JAK-2 substrate, JAK-2(a), is:

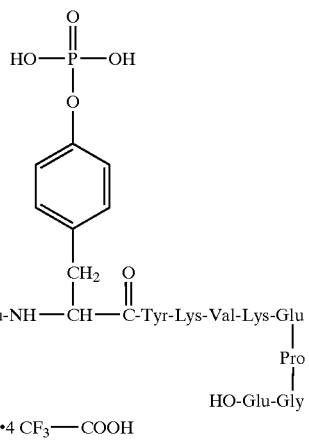

The formula of the second JAK-2 substrate, JAK-2(b) is:

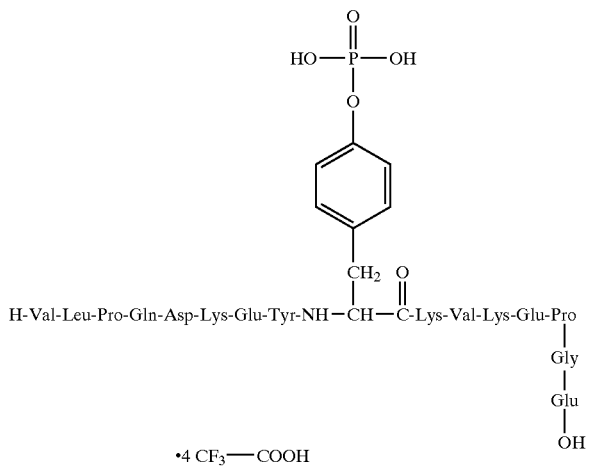

Both phosphorylated peptides displaced P-Tyr-F from the antibodies in a dose-dependent manner, whether measured by FP only (Sigma) or simultaneously using quenching or fluorescence polarization (MBL). The data were analyzed by nonlinear least squares analysis using equation 7, and the results are shown in FIGS. 6 and 7. The $K_i$s calculted from the fits are given in Table 3. The $K_i$s of the two phosphorylated JAK-2 kinase substrates for Sigma antibody were one and one-half orders of magnitude higher than those of the labelled ligands. Similar results were obtained for displacement from the MBL antibody as shown in FIG. 7, and the calculated $K_i$s for this antibody from both FP and quenching measurements were in good agreement. Thus, using the fluoresceinated phosphorylamino acids in a competition reaction to measure kinase and phosphatase activities requires that the concentrations of added fluoresceinated ligand should be comparable to $K_d$ and the amount of A up to 10×L. Under these degenerate conditions, the data can then be analyzed by Equation 4.

Discussion

Two superior anti-phosphotyrosine antibodies were identified that produced changes in the fluorescence polarization of a bound ligand or quenching of its emission intensity, and would enable quantitation of the activities of any phosphatase or kinase. Kinase phosphorylation of a substrate peptide or protein was monitored by specific displacement of a fluorescent phosphorylamino acid or a fluorescent phosphorylated peptide from an antibody by the reaction product from the kinase assay (see reaction scheme below). A proposed assay format for the fluorescent kinase assay is given below.

(21)

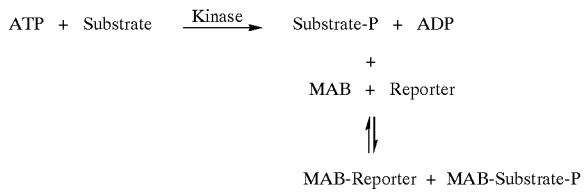

In this scheme, the kinase reaction proceeds for a period of time, is stopped by the addition of EDTA, and both antibody and fluoresceinated phosphorylamino acid added. Alternatively the antibody and labeled ligand could be present at time=0. The phosphorylated substrate would compete with the fluoresceinated phosphorylamino acid for the antibody, giving intermediate values of polarization and/or quenching. Phosphatase activity can also be monitored using this immunoassay. Several fluorescent substrates have previously been used to kinetically follow phosphatase activity. These include phosphotyrosine (Z. Y. Zhang et al., *Anal. Biochem.* 211:7–15 (1993); B. Galvan et al, *Clin. Biochem.* 29:125–131 (1996)), 2-methoxybenzoyl phosphate (P. Paoli et al., *Experientia* 51:57–62 (1995)), europium-labeled antibody (D. Worm, *Diabetologia* 39:142–148 (1996)); terbium chelates (T. K. Christopoulos, *Anal. Chem.* 64:342–346 (1992)), and fluorescein diphosphate (E. Tolsa et al., *J. Immunol. Methods* 192:165–172 (1996)), with fluorescein diphosphate being the most sensitive and amenable to HTS.

The evaluated antibodies demonstrated high affinities for the fluoresceinated phosphoryl amino acids. Therefore, a significant concentration of phosphorylated peptide would be required to displace the labeled ligand. This is detriment for kinase assays. However, this problem can be obviated by selecting three generic peptides, one for each of the three amino acids, that is phosphorylated and fluorescently labeled. Peptides having reduced affinity for the antibodies will allow detection of lower concentrations of phosphorylated product from the kinase reactions. With proper selection of the peptide and its fluorescent labeling, the assay format can be FP, FRET, FQ, or FCS.

Two anti-phosphoryltyrosine antibodies (Sigma, St. Louis, Mo., and MBL International Corp., Watertown, Mass.) were identified that produced robust fluorescence signals upon binding a labeled phosphoryltyrosine or phosphoryltyrosine peptide. The MBL antibody not only yielded a large polarization change, but also significantly quenched (i.e., reduced by 50%) the probe fluorescence. By using an antibody-reporter pair which, upon binding to each other, exhibit a change in both FP and FQ, the kinase assay described above can be performed in any fluorescent plate reader, not just those with polarization capabilities. The use of polarization as a readout is desirable since this parameter is independent of the fluorescence emission intensity (Leavine, L. M., et al., *Anal. Biochem.* 247:83–88 (1997)) and is thus not subject to the optical artifacts imparted by colored compounds which may quench the fluorescence emission of the label. Several other anti-phosphoryltyrosine antibodies from other suppliers were also tested (results not shown but the suppliers are listed in Materials and Methods) and found to produce low or inconsistent fluorescence changes upon binding the fluorescent ligand.

Four antibodies against phosphoserine and phosphothreonine (obtained from Sigma and Zymed) were tested. The Sigma antibodies against phosphoserine and phosphothreonine produced fluorescence polarization changes of sufficiently large dynamic range that the antibodies can easily be used to measure the activities of specific kinases.

All three fluorescein labelled phosphorylamino acids had higher affinities for their specific antibodies than their unlabeled counterparts, presumably due to their relatively small size and the increased hydrophobicity contributed by the fluorescein moiety. Due to the high affinity of the antibodies for the labeled phosphorylamino acids, a significant amount of product must be generated by kinase activity before displacement can occur. However, any labeled phosphorylated peptide or small protein, which would have lower affinity for the antibody could instead be used as the competitive ligand, including fluorescein-modified phosphorylated JAK-2 substrate peptides. Thus, the assay format gives the user a great deal of latitude for tailoring reagents and reaction conditions to meet the requirements of a specific kinase or phosphatase.

Example 2

Identification of Peptides having a Decreased Affinity for Antibody

Materials and Methods

Fluorescent Kinase Assay

As is discussed above, the displacement of reporter molecule by phosphorylated substrate in the competitive immunoassays of the invention will occur at lower concentrations of phosphorylated substrate, and thus most amenable to HTS, where the $K_d$ of the antibody for the phosphorylated substrate is less than or equal to the $K_d$ of the antibody for the reporter molecule. This may be accomplished by obtaining a small phosphorylated labeled peptide which has a lower binding affinity toward its antibody than the corresponding fluorescent phosphorylated amino acid (between about 0.5 nM and 1 nM for fluoresceinated phosphotyrosine or phosphoserine). Appropriate peptides may have between about 3 and 50 amino acid residues, preferably between about 3 and 25 residues, more preferably between about 3 and 15 residues, and most preferably between about 4 and 10 amino acid residues. Such peptides may be chemically synthesized, may be the result of enzymatic or chemical cleavage of a larger peptide or protein, or may be produced recombinantly. The peptides are then labeled and purified, and their affinities toward their corresponding antibodies are measured. Adjustments to the length and sequence of the peptides can be made to the peptides if this is deemed necessary as a result of their $K_d$ for antibody. Pentapeptides have been prepared which contain phosphorylated amino acids with a free cysteine available for labeling with a fluorophore. Peptides having the desired affinity (between about 50 nM and 100 nM) are then tested in the assay system for detecting the phosphorylation of substrate by kinases. As the assay is only measuring product, it will be possible to identify the actual amino acid of a substrate that is being phosphorylated by a kinase using cocompetition experiments. For example, a peptide substrate that has been phosphorylated by a kinase can be used to displace reporter peptides containing individual phosphorylated amino acids (i.e., either Ser, Thr or Tyr) from their respective antibodies.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

TABLE 1

Affinities of Anti-phosphoryltyrosine Antibodies for Fluoresceinated Phosphoryltyrosine

| | Fluorescence Polarization | | Fluorescence Quenching | |
|---|---|---|---|---|
| Antibody | $K_d$, nM sites (p)[1] | $\Delta p$[1] | $K_d$, nM Sites ($\Phi$)[2] | $Q_f/Q_b$[3] |
| Sigma | 1.9 ± 0.3 | x9 | — | — |
| Gibco BRL | 9.8 ± 7.3 | x6 | — | — |

TABLE 1-continued

Affinities of Anti-phosphoryltyrosine Antibodies for Fluoresceinated Phosphoryltyrosine

| | Fluorescence Polarization | | Fluorescence Quenching | |
|---|---|---|---|---|
| Antibody | $K_d$, nM sites (p)[1] | $\Delta p$[1] | $K_d$, nM Sites $(\Phi)$[2] | $Q_f/Q_b$[3] |
| ICN | 3.8 ± 1.0 | x6 | 5.1 ± 1.6 | 1.55 |
| UBI | bad data | x5 | 81.8 ± 52.1 | 1.55 |
| MBL | 4.7 ± 1.1 | x9 | 3.9 ± 0.3 | 2.05 |
| Zymed rabbit polyclonal | 6.6 ± 1.3 | x8 | 1.7 ± 0.7 | 1.28 |
| Zymed PY Plus | poor signal | x2 | 4.2 ± 2.7 | 1.1 |

[1]Direct polarization measurements
[2]$\Phi$ is the decreased Quantum Yield used to calculate the $K_d$
[3]Ratio of the Quantum Yields of free and bound probe. Used to correct polarization measurements as described in Data Analysis.

TABLE 2

Affinities of Anti-phosphorylserine and Anti-phosphorylthreonine Antibodies for Fluoresceinated Phosphorylamino Acids

| | Fluorescence Polarization | | |
|---|---|---|---|
| Antibody | $K_d$, nM Sites (p) | | $\Delta p$ |
| Sigma Anti P-Ser | 0.30 ± 0.03 | | x9 |
| Zymed Anti P-Ser | ≈8.13* | | x2.5 |
| Sigma Anti P-Thr | 1.055 ± 0.9 | | x5.1 |
| Zymed Anti P-thr | 58.1 ± 10.1 | | x5 |

*Signal too noisy for accurate quantitation

TABLE 3

Affinities of Unlabelled Phosphorylamino Acids and Phosphorylated JAK-2 Substrates for their Respective Antibodies[1]

| Phosphoryl | Sigma Monoclonal | | MBL Monoclonal | |
|---|---|---|---|---|
| Ligand | $K_d$, nM (p) | $K_d$, nM $\Phi$ | $K_d$, nM (p) | $K_d$, nM $\Phi$ |
| Phosphoryltyrosine | 11.9 ± 2.5 | — | 5.5 ± 1.0 | 5.4 ± 0.5 |
| Phosphorylserine | 16.8 ± 3.1 | — | — | — |
| Phosphorylthreonine | 44.1 ± 6.0 | — | — | — |
| JAK-2(a) | 15.4 ± 1.6 | — | 8.1 ± 1.8 | 11.6 ± 4.1 |
| JAK-2(b) | 49.5 ± 3.6 | — | 12.1 ± 1.1 | 8.1 ± 0.9 |

[1]$K_d$s are calculated for nM sites (i.e. - normality)

What is claimed is:

1. An article of manufacture comprising, packaged together:
   (i) a reporter molecule comprising a flourescent label and a phosphorylated amino acid,
   (ii) an antibody which selectively binds to a molecule comprising said phosphorylated amino acid; and
   (iii) a substrate molecule comprising the same amino acid molecule that is phosphorylated in said reporter molecule;
   wherein said substrate molecule is labeled with an acceptor fluorophore and wherein said antibody is labeled with a donor fluorophore which corresponds to the acceptor fluorophore labeling said substrate molecule.

2. The article of manufacture of claim 1 wherein said phosphorylated amino acid is selected from the group consisting of serine, threonine and tyrosine.

3. The article of manufacture of claim 1 further comprising an enzyme selected from the group consisting of kinases and phosphatases.

4. The article of manufacture of claim 3 wherein the enzyme is a kinase.

5. The article of manufacture of claim 3 wherein the enzyme is a phosphatase.

6. The article of manufacture of claim 1 further comprising a phosphate source.

7. The article of manufacture of claim 6 further comprising an enzyme selected from the group consisting of kinases and phosphatases.

8. The article of manufacture of claim 7 wherein the enzyme is a kinase.

9. The article of manufacture of claim 7 wherein the enzyme is a phosphatase.

10. The article of manufacture of claim 1 further comprising a phosphate acceptor.

11. The article of manufacture of claim 10 further comprising an enzyme selected from the group consisting of kinases and phosphatases.

12. The article of manufacture of claim 11 wherein the enzyme is a kinase.

13. The article of manufacture of claim 11 wherein the enzyme is a phosphatase.

14. An article of manufacture comprising, packaged together:
   (i) a reporter molecule comprising a flourescent label and a phosphorylated amino acid,
   (ii) an antibody which selectively binds to a molecule comprising said phosphorylated amino acid; and
   (iii) a substrate molecule comprising the same amino acid molecule that is phosphorylated in said reporter molecule;
   wherein said substrate molecule is labeled with an acceptor fluorophore and wherein said antibody is labeled with a acceptor fluorophore which corresponds to the donor fluorophore labeling said substrate.

15. The article of manufacture of claim 14 wherein said phosphorylated amino acid is selected from the group consisting of serine, threonine and tyrosine.

16. The article of manufacture of claim 14 further comprising an enzyme selected from the group consisting of kinases and phosphatases.

17. The article of manufacture of claim 16 wherein the enzyme is a kinase.

18. The article of manufacture of claim 16 wherein the enzyme is a phosphatase.

19. The article of manufacture of claim 14 further comprising a phosphate source.

20. The article of manufacture of claim 19 further comprising an enzyme selected from the group consisting of kinases and phosphatases.

21. The article of manufacture of claim 20 wherein the enzyme is a kinase.

22. The article of manufacture of claim 20 wherein the enzyme is a phosphatase.

23. The article of manufacture of claim 14 further comprising a phosphate acceptor.

24. The article of manufacture of claim 23 further comprising an enzyme selected from the group consisting of kinases and phosphatases.

25. The article of manufacture of claim 24 wherein the enzyme is a kinase.

26. The article of manufacture of claim 24 wherein the enzyme is a phosphatase.

* * * * *